US00PP31232P2

(12) United States Plant Patent
Warren

(10) Patent No.: US PP31,232 P2
(45) Date of Patent: Dec. 17, 2019

(54) CRABAPPLE TREE NAMED 'JFS KW139MX'

(50) Latin Name: *Malus*
Varietal Denomination: JFS KW139MX

(71) Applicant: J. Frank Schmidt & Son Co., Boring, OR (US)

(72) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 0 days.

(21) Appl. No.: 16/501,049

(22) Filed: Feb. 13, 2019

(51) Int. Cl.
*A01H 5/00* (2018.01)
*A01H 6/74* (2018.01)

(52) U.S. Cl.
USPC ..... Plt./173

(58) Field of Classification Search
USPC ..... Plt./173
CPC ..... A01H 5/00; A01H 6/74
See application file for complete search history.

*Primary Examiner* — Annette H Para
(74) *Attorney, Agent, or Firm* — Klarquist Sparkman, LLP

(57) ABSTRACT

A variety of crabapple which combines a combination of a tight upright oval growth habit, attractive red purple flowers, slightly glossy dark purple foliage in the spring and early summer, persistent small red fruit, and a strong resistance to the diseases fireblight and apple scab.

10 Drawing Sheets

Latin name of the genus and species of the plant claimed: *Malus*.

Variety denomination: 'JFS KW139MX'.

BACKGROUND OF THE INVENTION

In the summer of 2000, as part of my tree breeding and selection program, I selected a crabapple tree which I named 'KW-31MX' (unpatented). 'KW-31MX' was a green-leafed tree with white flowers which originated from open pollinated crabapple seed I had picked in the fall of 1994. 'KW-31MX' was a very promising tree, but I ultimately decided that it was not completely superior to existing commercial cultivars, so I decided to collect seed from it to continue my breeding line. I never introduced 'KW-31MX' and it was later destroyed. All of the above took place in a nursery in Boring, Oreg.

I collected open pollinated fruit from *Malus* 'KW-31MX' in the fall of 2000 and extracted seed and I sowed the seed in beds in the nursery in Boring, Oreg. The seed germinated in the spring of 2001 and grew well. In February of 2002, I dug the resulting seedlings and kept 404 of the most vigorous plants. In April of 2002, I transplanted these 404 open pollinated seedlings of 'KW-31MX' into another bed. During the spring and summer of 2002, I inoculated these seedlings with apple scab fungus and evaluated for resistance. In the fall of 2002, I marked the most promising 107 of these small trees which I dug, destroying the others. These 107 small trees were held in cold storage, then I transplanted the trees into a row in May 2003. I grew these trees in the nursery row for three seasons and evaluated them for form, flower quality, and disease resistance. In the fall of 2005, I marked the best 39 of these trees and destroyed the others. I dug these 39 trees and transplanted them into a nursery row on wider spacing in January, 2006. These 39 trees were evaluated for two more growing seasons, and by the fall of 2007 I had marked seven of these to be kept, destroying the others.

One of these seven trees is the subject of the current application and I named it 'JFS KW139MX'. It was selected and named because it possessed an outstanding and unique combination of bright reddish purple flowers, reddish purple new foliage color, extremely small red fruit, strong disease resistance, and a desirable upright oval growth habit.

I dug the seven aforementioned trees and in February of 2008 and I planted them into a long term experimental evaluation block on wide spacing. Of these remaining seven trees that derived from the open pollinated seed of 'KW-31MX', the present invention 'JFS KW139MX' was the only tree with reddish purple colored flowers and reddish purple new foliage color. The other six trees all had white flowers and green foliage color and all were subsequently destroyed and were never patented or introduced as cultivars. All of the above trees were grown and selected in the same Boring, Oreg. nursery.

In the summers of 2007, 2009, 2010, 2011, and 2014, I collected propagating wood from the original 'JFS KW139MX' tree and directed asexual propagation by budding onto *Malus* rootstock in small experimental plots in a Canby, Oreg. nursery. This propagation resulted in 8, 10, 5, 8, and 8 trees, respectively. I evaluated these propagated trees in subsequent years and determined that these asexually propagated plants show that the characteristics of my new tree are firmly fixed and identical to my original tree in every manner that has been observed. Of these propagated trees, one was planted in a long term evaluation block in the Boring, Oreg. nursery in February 2013.

BRIEF SUMMARY OF THE INVENTION

This new cultivar possesses a unique combination of characteristics that have proven firmly fixed in asexually propagated progeny and that comprise a combination of a upright oval growth habit, a consistent branch angle on two year old nursery trees, attractive reddish purple flowers, reddish purple spring foliage, unusually small persistent fruit, and strong resistance to the diseases fireblight and apple scab.

For testing purposes only, four trees were sent, two each, to cooperators in Ohio and North Carolina in 2011, and four trees were sent, two each, to cooperators in New York and Wisconsin in 2013. These trees were sent under the conditions of a non-propagation and non-distribution agreement. In the Spring of 2018 the land where the original 'JFS KW139MX' tree stood had to be cleared for future plantings, and the original 'JFS KW139MX' tree was destroyed.

BRIEF DESCRIPTION OF THE DRAWING

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
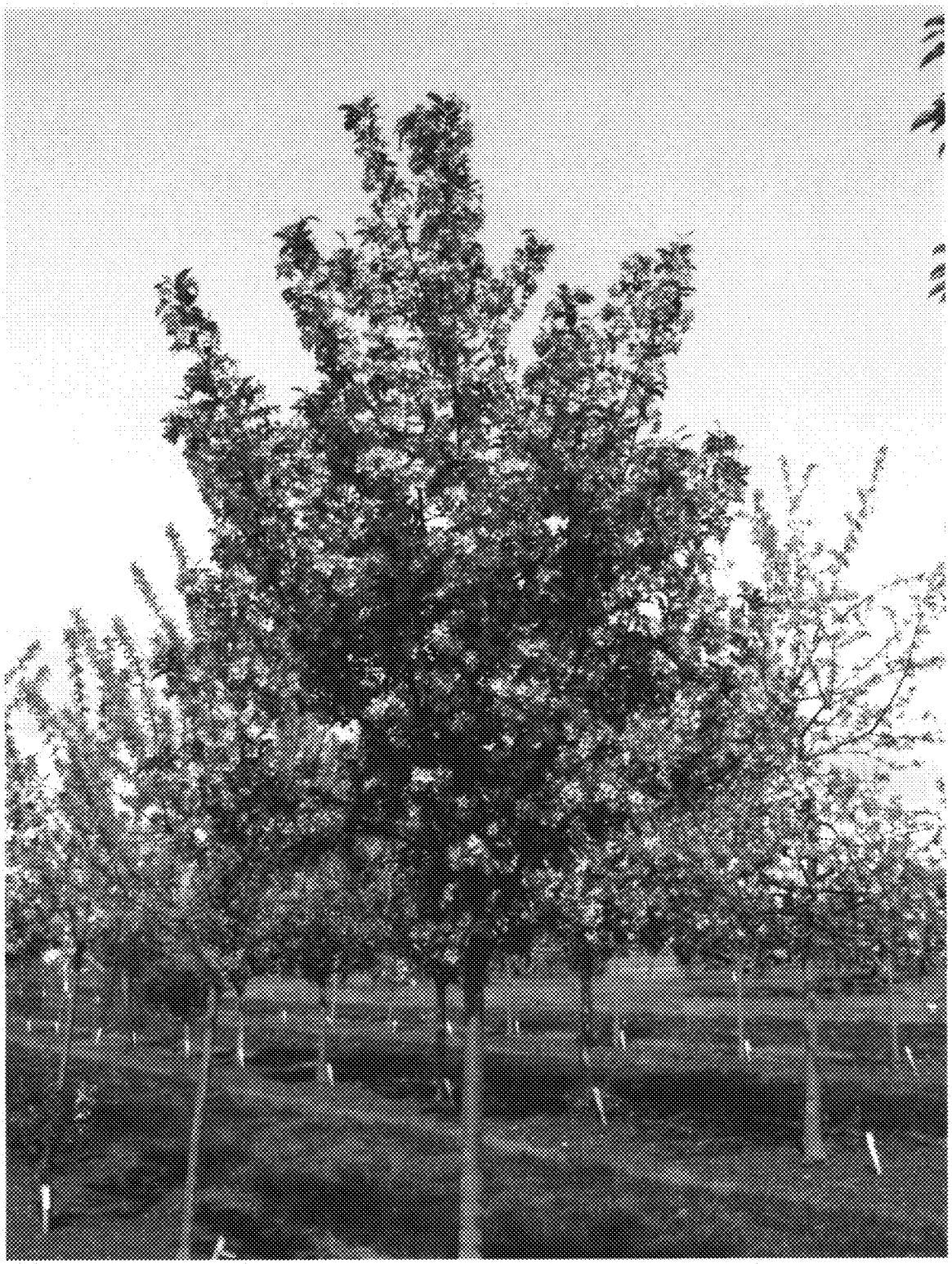
FIG. 1: Shows the original tree in flower at 6 years of age with emerging foliage
Figure 2:
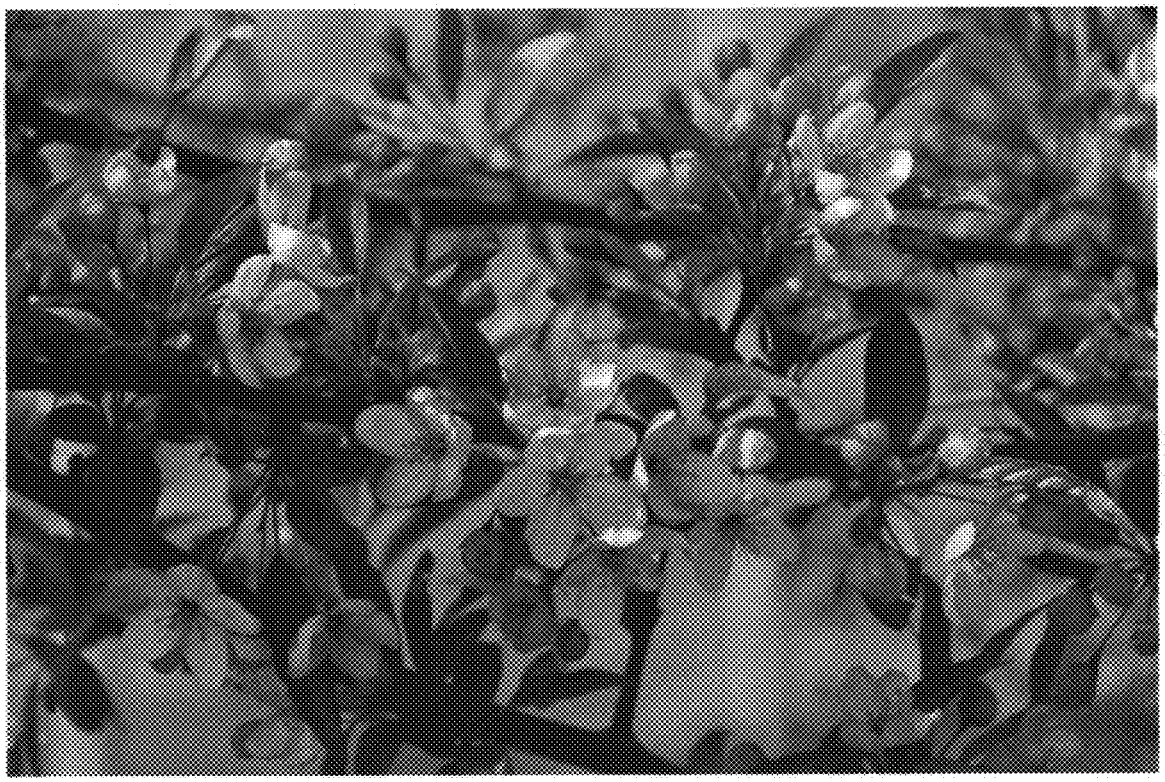
FIG. 2: Shows a close-up of the flowers on the original tree.
Figure 3:
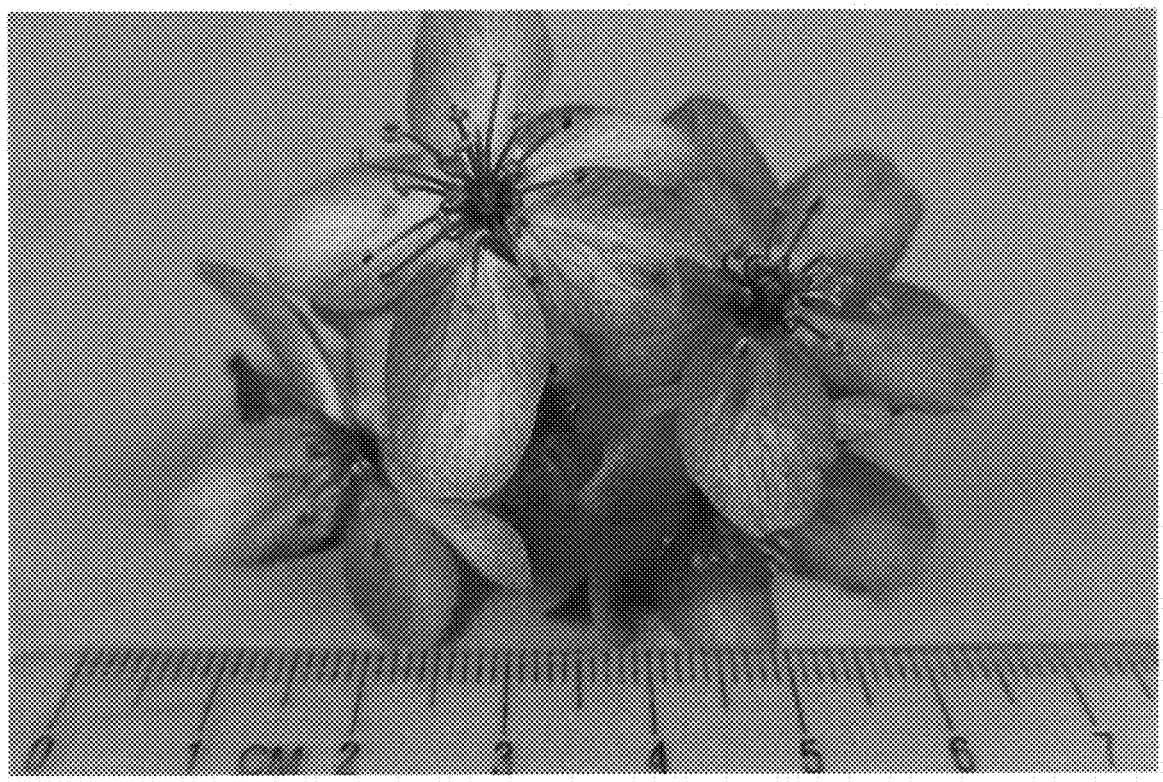
FIG. 3: Shows a close up of a few flowers on a display board with a scale.
Figure 4:
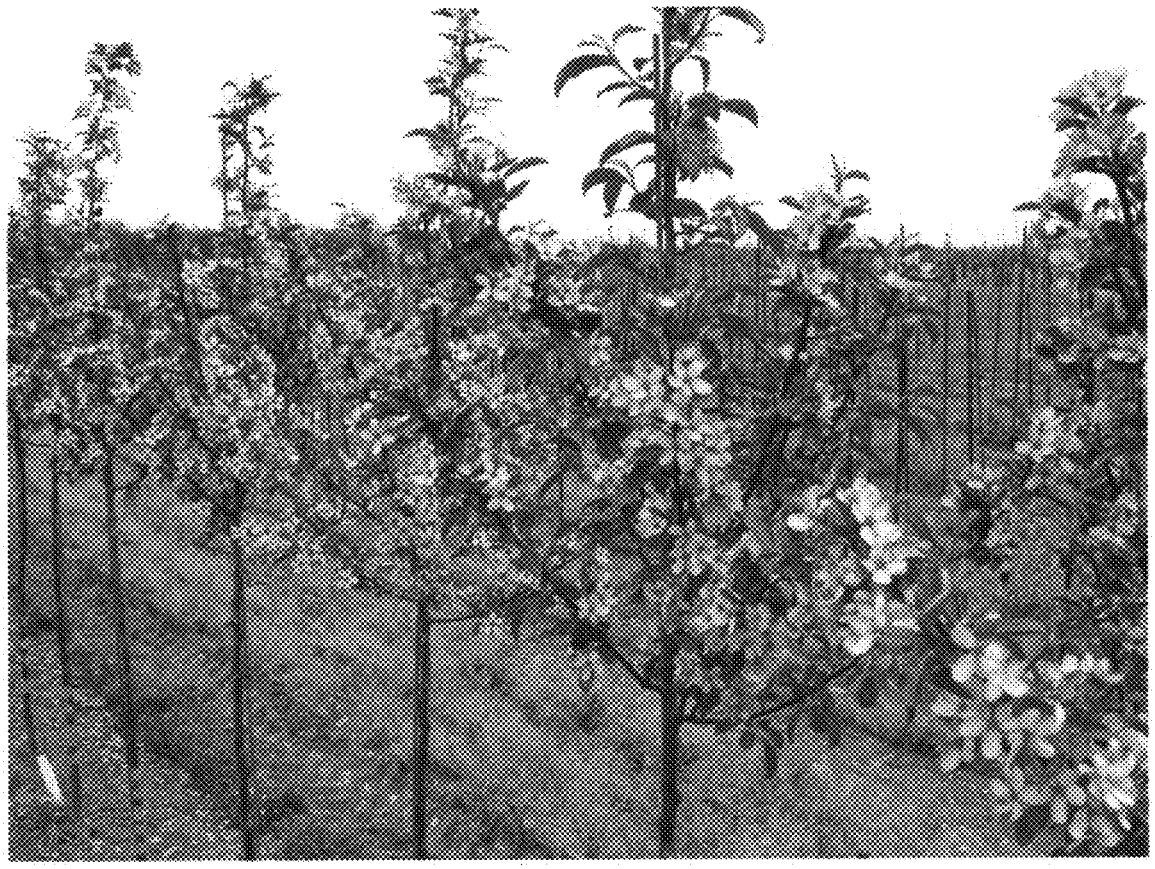
FIG. 4: Shows 2 year old trial trees in flower.
Figure 5:
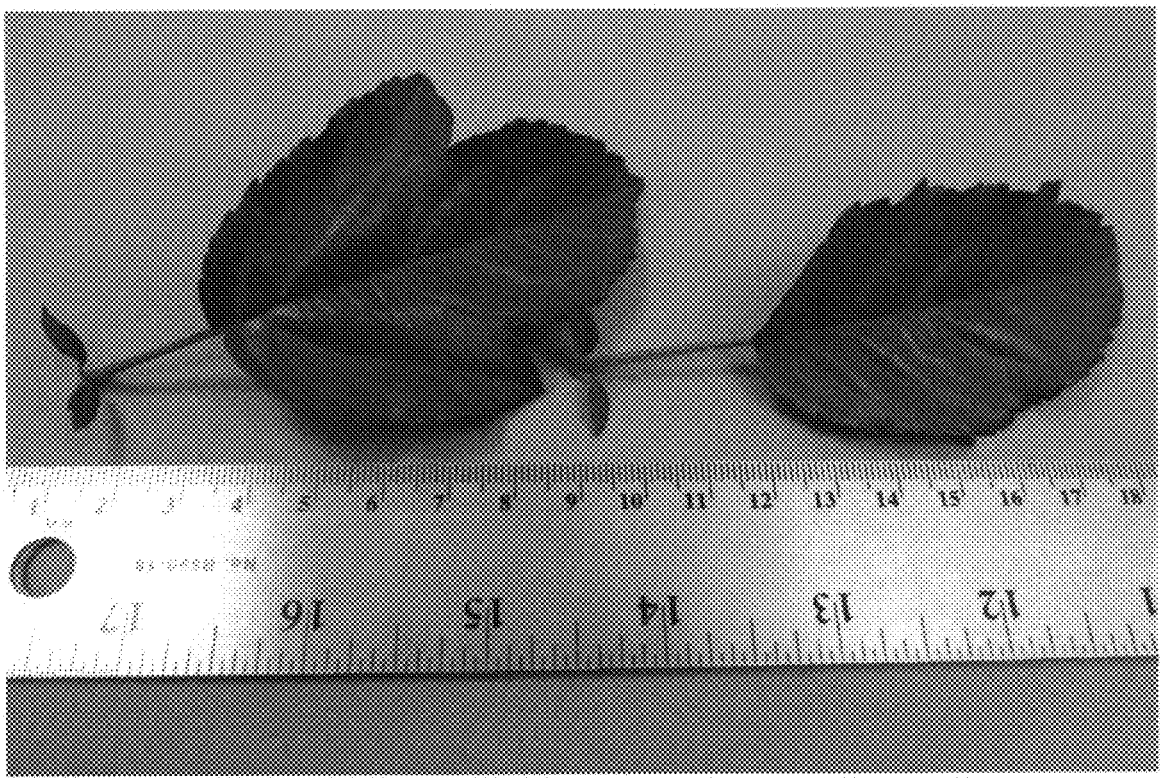
FIG. 5: Shows mid-summer foliage on a display board with scale.
Figure 6:
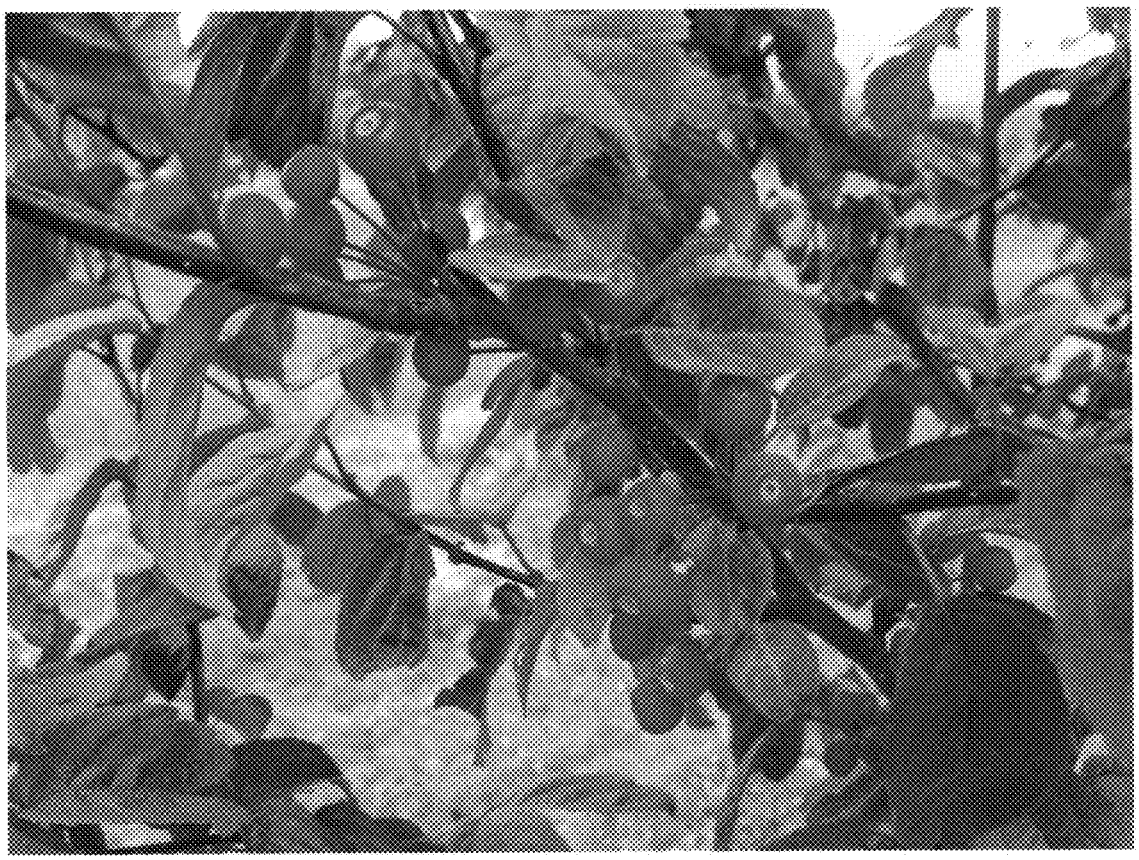
FIG. 6: Shows a close up of the original tree at 8 years of age with fruit
Figure 7:
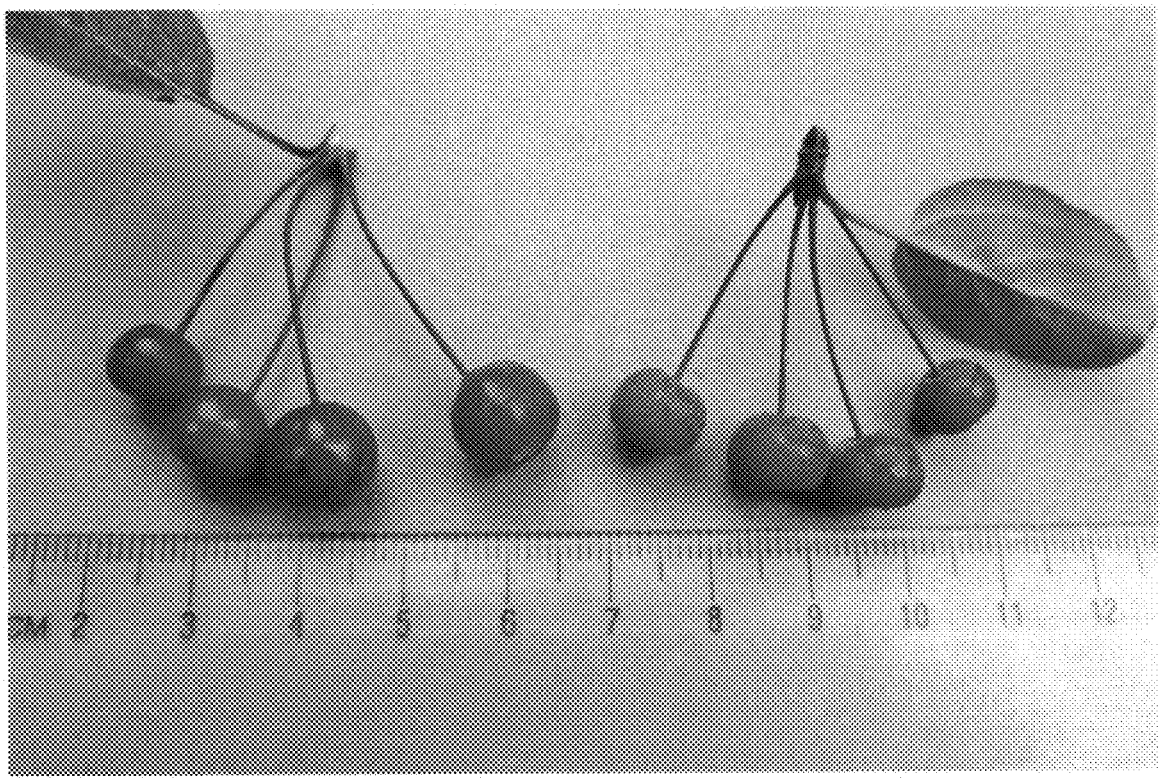
FIG. 7: Shows a close-up of fruit on a display board with a scale.
Figure 8:
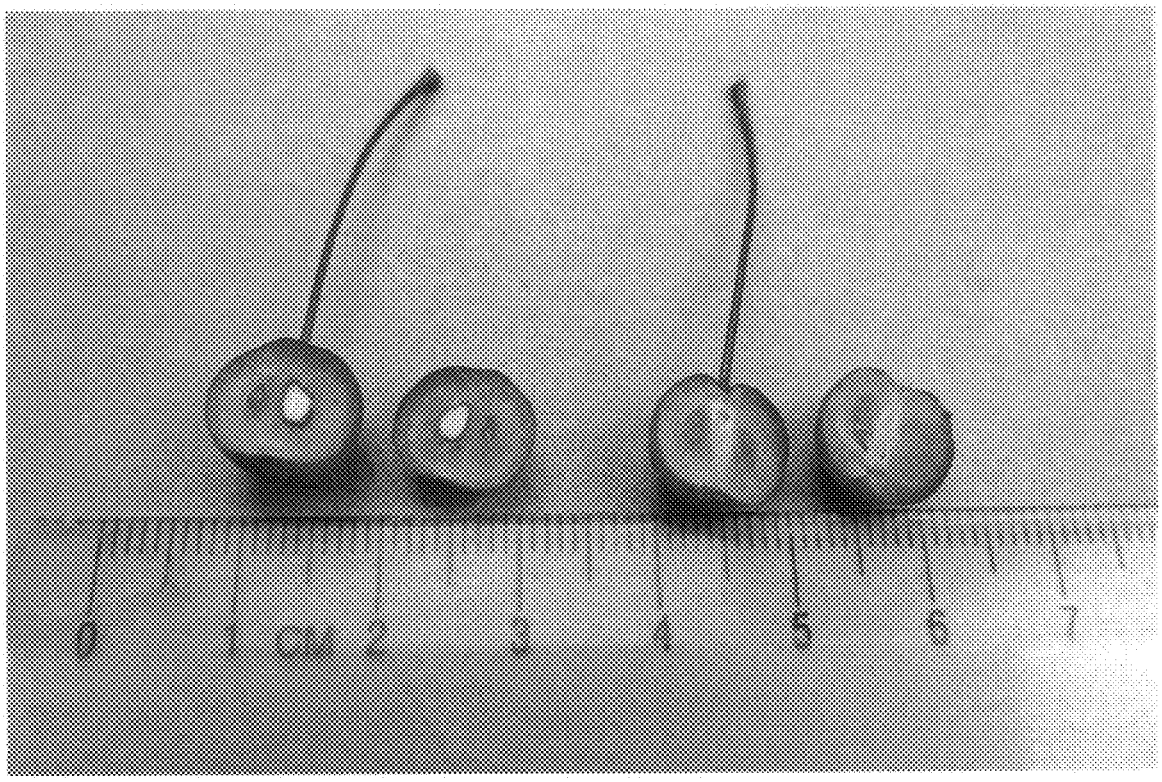
FIG. 8: Shows a close-up of fruit halved on a display board with a scale.
Figure 9:
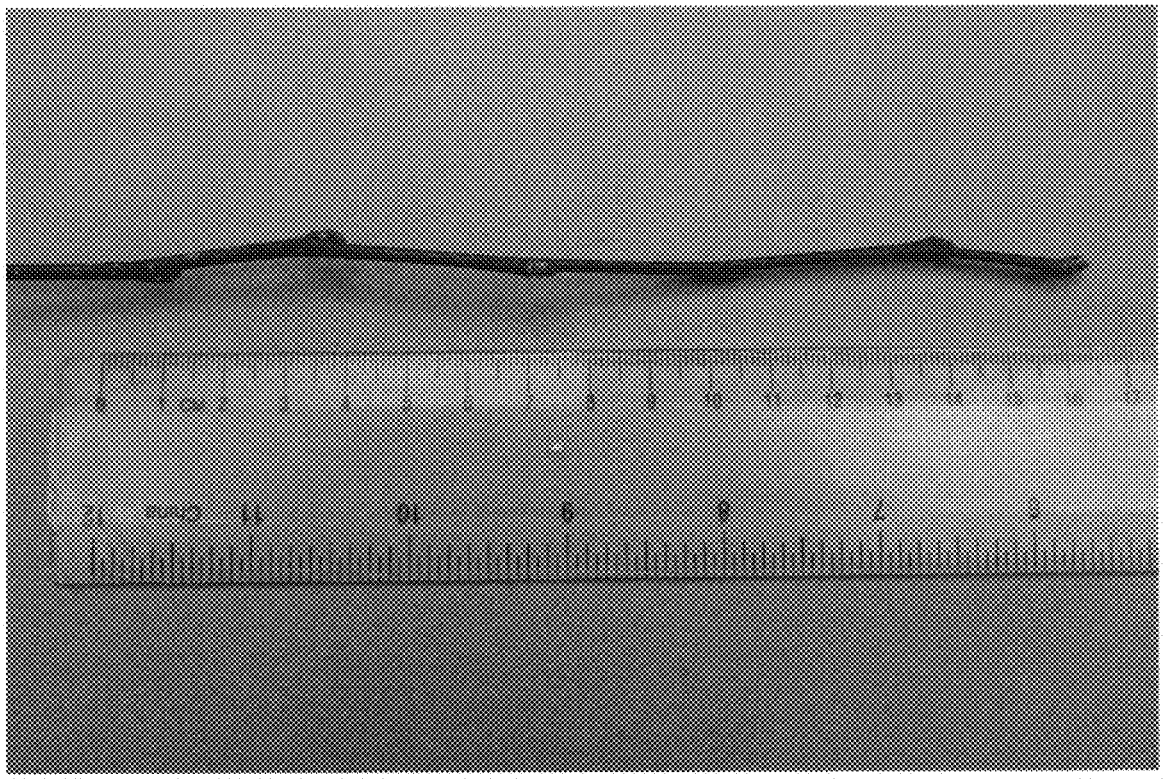
FIG. 9: Shows a dormant branch tip on a display board with a scale.
Figure 10:
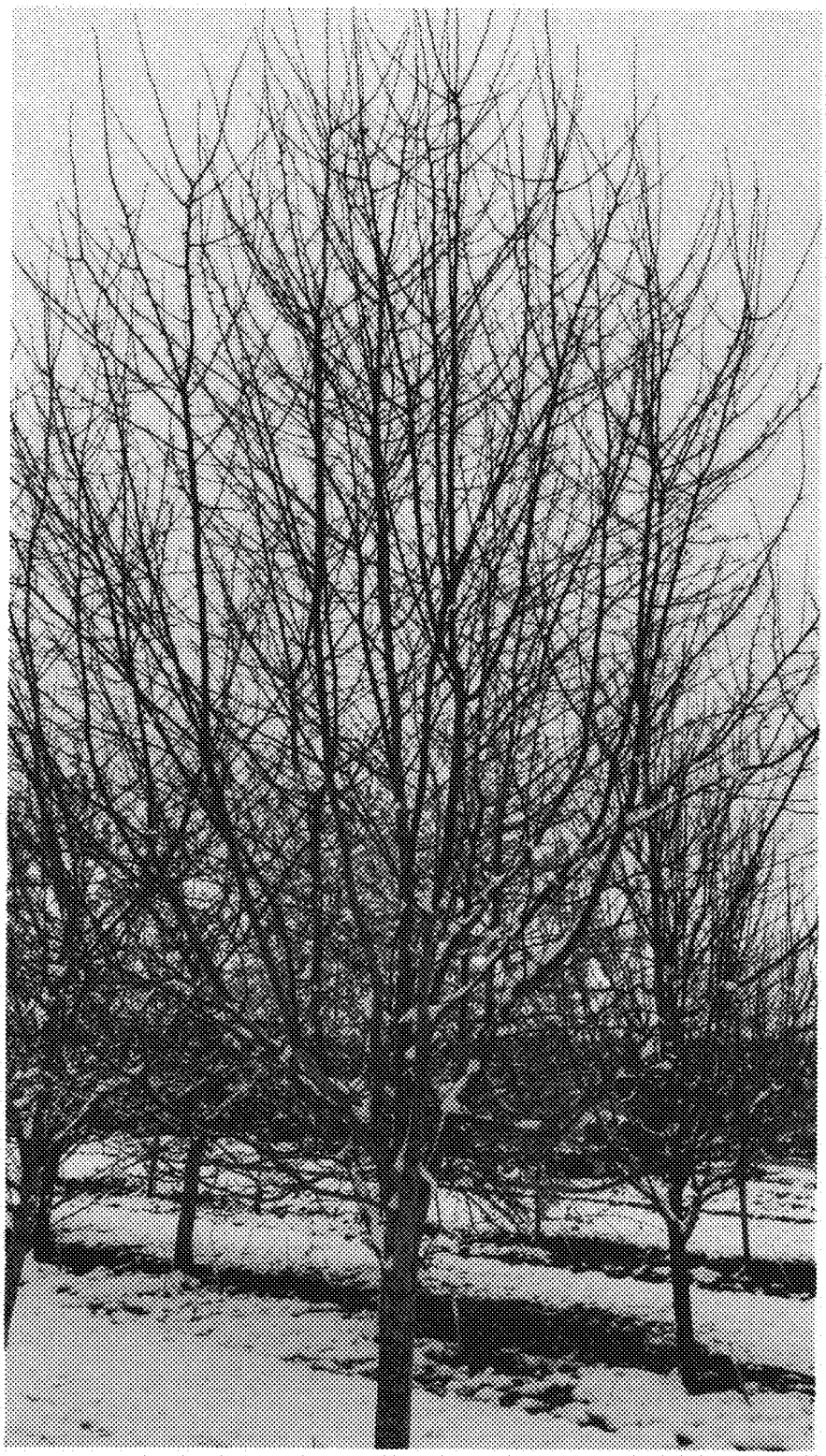
FIG. 10: Shows a tree at 8 years of age without foliage during the winter.

The following detailed description of the 'JFS KW139MX' variety is based on observations of the original tree growing in Boring, Oreg. and of two and three year old asexually reproduced progeny. The observed progeny were trees which were growing in Canby, Oreg. Color descriptions are made with reference to The Royal Horticultural Society (London) Colour Chart© 1986, except where ordinary dictionary significance of color is indicated.

Scientific name: *Malus* 'JFS KW139MX'.

Parentage:

*Seed parent*.—Open pollinated seedling of *Malus* 'KW-31MX'.

*Pollen parent*.—Unknown.

Tree:

*Overall shape*.—Upright oval.

*Height*.—At 8 years of age, about 6 meters high.

*Width*.—At 8 years of age 3 meters spread.

*Caliper* (*trunk diameter*).—At 8 years of age, about 106 mm at 100 mm height, 96 mm at 1 m height.

*Trunk*.—Strong and straight under nursery growing conditions.

*Trunk bark texture*.—Smooth, some vertical fissures with age.

*Trunk bark color*.—Grey Brown 199A to Brown 200D.

*Immature bark color*.—Red Purple 71A.

*Mature bark color*.—Purple 79C to Purple 77C.

*Lenticels*.—Elongated to oval 0.75 mm×0.25 mm. Greyed Yellow 161A in color.

*Branch color*.—Purple 79A to Violet 86A.

*Branch lenticels*.—Similar to those on the trunk.

*Dormant buds*.—Elongated oval with acute tip, imbricate scales, 2 mm×4 mm.

*Internodes*.—Average internode length is about 35-40 mm on a one-year old shoots.

*Hardiness*.—Has tolerated temperatures to 10 degrees F. in Boring Oreg. which is the lowest temperature experienced in this location. It is believed to have zone 4 cold hardiness similar to other plants of the same species.

*Disease resistance*.—Excellent resistance to fireblight, powdery mildew & apple scab on foliage and fruit.

Leaves: Except as otherwise noted, observations are from twenty vigorous growth leaves.

*Arrangement*.—Alternate.

*Type*.—Simple, entire, or with 1 to 2 lobes.

*Texture*.—Smooth, with slight undulation between the veins.

*Sheen*.—Glossy.

*Length*.—Averaging 90 mm-110 mm.

*Width*.—Averaging 4 5mm to 55 mm.

*Petioles*.—20 mm to 25 mm long, about 1-2 mm in diameter.

*Overall shape*.—Ovate, sometimes with 1 or 2 side lobes.

*Margin*.—Serrulate.

*Tip*.—Acute.

*Base*.—Broadly acute to rounded.

*Stipules*.—Two per leaf, 10 mm to 15 mm long by 2 mm to 3 mm wide.

*Spring leaf color*.—Greyed Purple 187A.

*Summer leaf color*.—Upper leaf surface: Greyed Purple 187A to 187D turning to Green 139A with age by midsummer. Lower leaf surface: Greyed Purple 183A to Greyed Purple 184A. Vein: Red Purple 59A to 59B.

*Fall leaf color*.—Foliage turns Orange Red 31A to Orange Red 34A.

*Fall color begins*.—November 1$^{st}$ (Boring, Oreg. 2018).

*Fall color peak*.—November 20$^{th}$ (Boring, Oreg. 2018).

*Fall color ends*.—December 1st (Boring, Oreg. 2018).

*Pubescence*.—None.

*Persistence*.—Tree is deciduous.

Flowers:

*Overall*.—Number of flowers per cluster: 5 to 6.

*Shape*.—Symmetrical, rounded, 5 petals, not cupped.

*Size*.—Approximately 32 mm to 37 mm in diameter.

*Unopened bud*.—Red Purple 60A to Red Purple 60C.

*Petals*.—Five petals per flower, 7 mm to 80 mm wide×15 to 17 mm long. Color Red Purple 60C fading to 62C.

*Sepals*.—Acute, length 2 mm×4 mm at base. Red Purple 60B.

*Stamen*.—About 18 to 22 stamens, 6 mm to 8 mm arranged concentrically around pistil. Red Purple 63A.

*Anthers*.—Greyed Orange 164A. 1 mm to 1.5 mm long by 0.25 mm to 0.5 mm in diameter.

*Pistil*.—Red Purple 62C compound, 3 to 5 branched, length 4 mm-7 mm. Ovary inferior, typically five carpels.

*Pollen*.—Yellow Orange 22C.

*Pedicel*.—28 mm to 34 mm long by 0.4 mm to 0.5 mm in diameter. Red Purple 60A to 60B.

*Pubescence*.—Yes on the upper side of the sepal.

*Fragrance*.—Slightly sweet.

*Flowering date*.—In Boring, Oreg. 2018. First bloom April 8th, peak bloom April 14th, last bloom May 1st.

Fruit: Observations are from a sampling of typical fruit.

*Cluster*.—3 to 5 fruits per cluster.

*Size*.—Typical fruit is 8 mm to 10 mm in diameter by 7 mm to 8 mm long.

*Shape*.—Flattened oval, wider than long.

*Skin*.—Smooth.

*Lenticels*.—None observed.

*Color*.—Immature summer fruit is Yellow Green 145A ripening to Red 46A to 43B in October.

*Seeds*.—Typically 2-3 per fruit, ovoid to rounded, 3 mm long and about 2 mm wide with a smooth surface, Greyed Orange 164A to Greyed Orange 164B in color.

*Fruit production*.—Moderate to heavy depending on the year.

*Fruit persistence*.—90% still persistent Nov. 20, 2018.

*Usage*.—Ornamental, non-edible.

COMPARISON TO THE SEED PARENT

Compared to the seed parent tree 'KW-31MX', my new cultivar, 'JFS KW139MX', has fruit which is 7-8 mm in diameter, ripens to Red 46A to Red 43B and persists with good ornamental quality. 'KW-31MX' has 10-12 mm diameter fruit that ripens to yellow. In addition, 'JFS KW139MX' has Greyed Purple 187A to 187D summer foliage, 'KW-31MX' has green foliage.

COMPARISON TO OTHER SIMILAR VARIETIES:

| | *Malus* 'JFS KW139MX' | *Malus* 'Durleo' U.S. Plant Pat. No. 20,167 | *Malus* 'Purple Prince' U.S. Plant Pat. No. 8,478 |
|---|---|---|---|
| Form | Upright tight oval | Compact upright oval. | Rounded |
| Leaf Length | 90 mm to 110 mm | 85 mm | 90 mm to 120 mm |

-continued

COMPARISON TO OTHER SIMILAR VARIETIES:

| | *Malus* 'JFS KW139MX' | *Malus* 'Durleo' U.S. Plant Pat. No. 20,167 | *Malus* 'Purple Prince' U.S. Plant Pat. No. 8,478 |
|---|---|---|---|
| Leaf Width | 45 mm to 55 mm | 43 mm | 50 mm to 75 mm |
| Petiole | 20-25 mm | 27 mm | 20 mm-30 mm |
| Spring Upper Leaf Color | Greyed Purple 187A | Green 143B | Red Purple 60A |
| Branch Color | Purple 79A to Violet 86A | Greyed Purple 183B | Purple 176A to 177A |
| Bark on trunk | Smooth, some vertical fissures. | Bole like bumps | Becomes rough with age some vertical fissures |
| Branch Angle on 2YR Trees | 40-50 degrees | 60-70 degrees | 30-60 degrees |
| Fruit Color | Red 46A to Red 43B | Red Purple 59A | Purple 185A |
| Fruit Size | 7 to 8 mm long × 8-9 mm wide | 10 mm × 10 mm | 12 to 15 mm × 12-15 mm |
| Fruit Shape | Flattened oval, wider than long | Round | Round |

COMPARISON OF AVERAGE INTERNODE LENGTH

When compared to the following commercial ornamental crab apple varieties 'JFS KW139' has longer average internode lengths.

| Cultivar | Average internode length |
|---|---|
| *Malus* 'JFS KW139MX' | 35-40 mm |
| *Malus* 'JFS-KW5' (U.S. Plant Pat. No. 14,375) | 25-30 mm |
| *Malus* 'Purple Prince' (U.S. Plant Pat. No. 8,478) | 30-35 mm |
| *Malus* 'Perfect Purple' (unpatented) | 25-30 mm |
| *Malus* 'Spring Snow' (unpatented) | 30-35 mm |
| *Malus* 'Prairiefire' (unpatented) | 30-35 mm |
| *Malus* 'Profusion' (unpatented) | 25-30 mm |

I claim:

1. A new and distinct variety of crabapple tree, as herein illustrated and described.

* * * * *